United States Patent [19]

Stöber

[11] Patent Number: 4,759,752
[45] Date of Patent: Jul. 26, 1988

[54] CATHETER

[75] Inventor: Herbert Stöber, Uber dem Rotter, Fed. Rep. of Germany

[73] Assignee: Intermedicat, Emmenbrucke, Switzerland

[21] Appl. No.: 930,784

[22] Filed: Nov. 14, 1986

[30] Foreign Application Priority Data

Nov. 19, 1985 [DE] Fed. Rep. of Germany ....... 3540949

[51] Int. Cl.$^4$ ............................................. A61M 5/00
[52] U.S. Cl. ........................................ 604/247; 604/9; 604/256; 604/34; 137/853; 251/342
[58] Field of Search ................... 604/247, 9, 99, 246, 604/256, 34, 250, 10, 129; 137/853, 859, 860; 251/342

[56] References Cited

U.S. PATENT DOCUMENTS

| | | | |
|---|---|---|---|
| 3,384,113 | 5/1968 | Pennisi | 137/853 |
| 3,534,771 | 10/1970 | Eyerdam et al. | 251/342 |
| 3,965,930 | 6/1976 | Nicholls | 137/853 |
| 4,346,704 | 8/1982 | Kulle | 604/247 |
| 4,445,896 | 5/1984 | Gianturco | 604/256 |
| 4,657,536 | 4/1987 | Dorman | 604/247 |

FOREIGN PATENT DOCUMENTS 3035748 5/1982 Fed. Rep. of Germany ...... 604/247

Primary Examiner—C. Fred Rosenbaum
Assistant Examiner—Denis Whelton
Attorney, Agent, or Firm—Spensley Horn Jubas & Lubitz

[57] ABSTRACT

A catheter having a proximal end provided with a non-return valve consisting of the catheter tubing end and of a rigid insert body whose rearward end is fixed in the catheter tubing. Bypass channels extend passed the end. The front end of the insert body is a cylindrical plug whose peripheral surface is joined by the catheter end acting as a valve hose. In case of overpressure in the catheter tubing, the tubing end is lifted from the plug and the pressure medium may escape accordingly.

5 Claims, 1 Drawing Sheet

CATHETER

BACKGROUND OF THE INVENTION

1. Field of the Invention

The present invention relates to a catheter and in particular to a catheter having a nonreturn valve which inhibits penetration of fluid and which opens in case of internal overpressure.

2. Description of Related Art

A catheter including a nonreturn valve is known (European Patent No. 0 018 179) which comprises a flexible tubular sleeve laterally surrounding the catheter head. The end of the catheter lumen is firmly closed by a plug which is anchored by a lateral adapter in a hole of the catheter tube. The flexible sleeve covers lateral holes of the catheter tubing. In case of overpressure in the catheter lumen, the flexible sleeve is partly lifted from the hose so that fluid may flow from the interior of the catheter tubing through the enlarged flexible sleeve to the outside. Due to the sealing effect of the sleeve which flexibly adjoins the catheter tubing, fluid is prevented from entering into the catheter head.

The production of such a nonreturn valve is expensive because, for closing the catheter end, a separate member is required which, with respect to the catheter tubing, has to act as a seal, and because radial openings must be provided at the catheter tube. Because of the use of cooperating flexible elements, namely the catheter tubing and the sleeve, the required sealing and opening behavior of the valve may be achieved only with difficulty. Further, during the assembly of the valve, it is difficult to slip the flexible sleeve over the catheter tubing, which is itself flexible.

It is therefore an object of the present invention to provide a catheter having a nonreturn valve which may be simply produced and in which the nonreturn valve has a reproducible, well-defined behavior in operation.

SUMMARY OF THE INVENTION

According to the invention the nonreturn valve comprises an elongated rigid insert body whose rear end is fixed to the catheter tubing. At least one bypass channel extending past the rear end of the insert body is provided. At the front end of the insert body is a plug about which the catheter tubing is flexibly and sealingly clamped to form the valve outlet.

The total nonreturn valve of the catheter of the present invention is located within the outer contour of the catheter tubing. In the nonreturn valve region, there are no radial holes in the catheter tubing. The flexibility properties of the catheter tubing are utilized to form the valve sleeve, which may be expanded in case of an internal pressure. The flexibility of the catheter tubing is harmonized with the oversize of the insert body relative to the internal diameter of the catheter tubing, such that the valve is opened in the case of a relatively low internal pressure in the catheter tubing, i.e. the catheter tubing is lifted, at least sectionwise, from the plug. The catheter head by itself forms the external valve hose of the nonreturn valve, with the valve opening being at the front end of the catheter tubing.

A particular advantage of the present invention resides in the use of a rigid insert body so that the flexible catheter tubing cooperates with and firmly encloses the rigid member. By this means, the resultant valve behavior is reproducible. To form the nonreturn valve, only one additional element is needed, namely the rigid insert body, which may be introduced relatively easily into the catheter tubing. Thus, it is not necessary to slip two flexible tubings over one another. Further, the external diameter of the catheter in the nonreturn valve region is not enlarged, or enlarged only to a slight extent.

In a preferred embodiment of the invention, a central portion intermediate the rear and front ends of the insert body is provided with radial projections to support the catheter tubing while longitudinal channels are left free. In this connection, the rearward end portion of the insert body serves as a fixing element which, however, does not completely block the catheter lumen. While the diameter of the central portion is inferior to that of the catheter, said central portion may be provided with radially projecting ribs to support the catheter.

The front end of the insert body is preferably designed as a round cupola extending beyond the end of the catheter tubing. The infusion fluid is discharged around said round cupola from the end of the catheter tubing. Furthermore, the round cupola of the insert body forms the front end of the catheter. Due to the round cupola shape, the body of the patient will not be injured when the catheter is introduced.

BRIEF DESCRIPTION OF THE DRAWINGS

A detailed description of the invention will be made with reference to the accompanying drawings, wherein like numerals designate corresponding parts in the several figures.

DESCRIPTION OF PREFERRED EMBODIMENTS

The following detailed description is of the best presently contemplated mode of carrying out the invention. This description is not to be taken in a limiting sense, but is made merely for the purpose of illustrating the general principles of the invention. The scope of the invention is defined by the appended claims.

Figure 1:
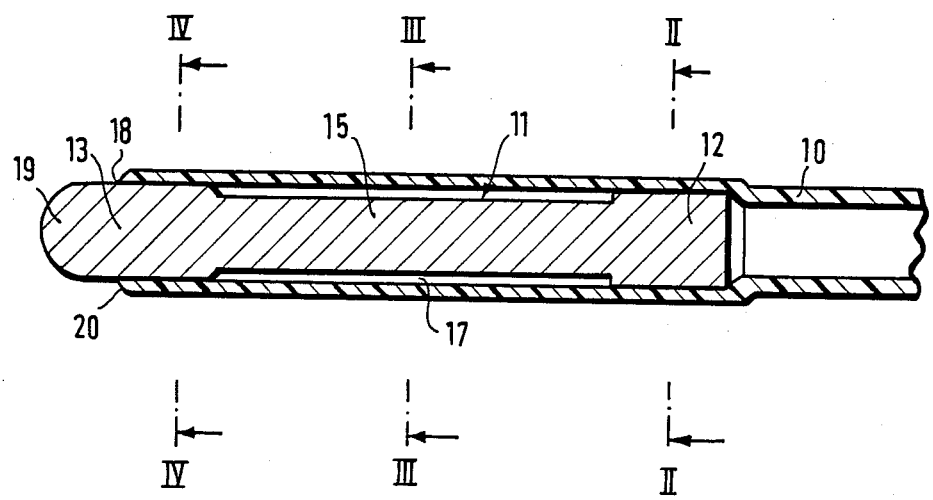
FIG. 1 is a longitudinal section of one embodiment of the present invention, illustrating a nonreturn valve mounted at a catheter head.
Figure 4:
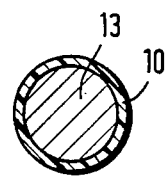
FIG. 4 is a cross section along line IV—IV of FIG. 1.
Figure 2:
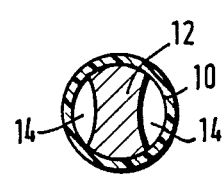
FIG. 2 is a cross section along line II—II of FIG. 1.

As shown in FIG. 1, the catheter tubing 10 consists of a tissue-compatible flexible material. The insert body 11 is slipped into the front end of the catheter tubing 10. The rear end of the longitudinal insert body 11 contains a fixation portion 12 and the front end is designed as a plug 13. The cross section of the rear end 12 is illustrated in FIG. 2. End 12 is substantially cylindrical, and flattenings are provided at opposite sides to form longitudinal channels 14 between the insert body 11 and the wall of the catheter tubing 10. The peripheral regions of end 12 which are in contact with the catheter tubing 10 slightly expand the catheter tubing 10, thus ensuring by friction a safe positioning of the insert body 11 inside the catheter hose 10. The fixation of the insert body 11 in the catheter tubing may also be realized by bonding or by other connection techniques.

Figure 3:
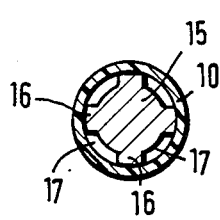
FIG. 3 is a cross section along line II—III of FIG. 1.

The central portion 15 of the insert body 11 extends between end 12 and front plug 13. As illustrated in FIG. 3, the central portion 15 of the insert body 11 has a cross section which is smaller than that of the catheter lumen. The radial stems 16 which radially extend from a cylindrical core are distributed peripherally and serve as the lateral support of the wall of the catheter tubing 10. The throughflow of infusion liquid is ensured through longitudinal channels 17 provided between the stems 16.

Plug 13 forming the front end of the insert body 11 is cylindrical, and the front end of the catheter tubing 10 is adjoined to its outer surface under radial tension. The catheter tubing 10 may be either not fixed or fixed only intermittently on plug 13, thus allowing its lifting, at least in part, from the periphery of plug 13 in case of an overpressure inside the catheter tubing. If so, the pressurized medium may escape through the front end 18 around the plug 13.

Plug 13 extends beyond the front end 18 of the catheter tubing, and its end is rounded.

The insert body 11 may be made of one piece of solid material; e.g., of plastic. The maximum external diameter of the rearward region 12 and of the central region 15 are substantially equal to the external diameter of plug 13. Said external diameter is slightly larger than the internal diameter of the catheter tubing 10 which, by this means, is slightly expanded by the insert body 11.

The front edge 20 of the catheter tubing 10 is sloped outwardly, thus forming a lip which adjoins plug 13 and further intensifying the sealing effect against external pressure.

An infusion solution provided to be administered to the patient is introduced into the catheter to flow through the longitudinal channels 14 past the rearward end 12 of the insert body into the longitudinal channels 17 of the central portion 15. Due to the pressure existing in the catheter, the front end of the catheter tubing is lifted from plug 13 so that the infusion solution may escape at the end of the catheter tubing. On the other hand, because of the sealing effect of the front catheter end encompassing plug 13, body fluid may not penetrate into the catheter tubing.

It will therefore be recognized that the present invention may be embodied in a variety of specific forms. The foregoing disclosed embodiment is therefore to be considered in all respects as illustrative and not restrictive, the scope of the invention being indicated by the appended claims, rather than the foregoing description, and all variations which come within the meaning and range of equivalency of the claims are intended to be embraced therein.

What is claimed is:

1. A catheter nonreturn valve which inhibits penetration of liquid and which opens in case of internal overpressure, said catheter nonreturn valve comprising:
    a catheter tubing including a forward, working end and having an internal diameter and an external diameter,
    an insert body configured to be inserted in the forward, working end of the catheter tubing, said insert body comprising;
    a front segment having a cross section, the front segment cross section having a diameter greater than the internal diameter of the catheter tubing, the front segment and the catheter tubing thereby defining a valve outlet which opens in case of internal overpressure,
    an end segment having a cross section and being fixed to the catheter tubing, the end segment cross section having a maximum diameter substantially equal to the diameter of the front segment cross section, the end segment having defined therein at least one bypass channel extending toward the front segment,
    a central segment intermediate the front segment and the end segment, the central segment having a cross section which is, at least in part, smaller in diameter than the diameter of the front segment cross section and the maximum diameter of the end segment cross section,
    wherein the external diameter of the catheter nonreturn valve is substantially equal to the external diameter of the catheter tubing.

2. A catheter according to claim 1 wherein the central segment of the insert body further includes a plurality of radial stems positioned to support the catheter tubing, the radial stems and the catheter tubing defining longitudinal channels therebetween.

3. A catheter according to claim 1 wherein the front segment of the insert body includes a round cupola, said cupola positioned to project beyond the forward, working end of the catheter tubing.

4. A catheter according to claim 1 wherein the at least one bypass channel extending toward the front segment comprises a lateral flattening or groove defined in the end segment.

5. A catheter according to claim 1 wherein the forward, working end of the catheter tubing has a front edge and wherein the front edge of the catheter tubing is bevelled inwardly.

* * * * *